United States Patent
Chigondo et al.

(10) Patent No.: US 10,570,160 B2
(45) Date of Patent: Feb. 25, 2020

(54) METHOD FOR THE SELECTIVE SYNTHESIS OF TRIALKOXYSILANES

(71) Applicant: Nelson Mandela Metropolitan University, Port Elizabeth (ZA)

(72) Inventors: Fidelis Chigondo, Gweru (ZW); Paul Watts, Port Elizabeth (ZA)

(73) Assignee: Nelson Mandela Metropolitan University, Port Elizabeth (ZA)

( * ) Notice: Subject to any disclaimer, the term of this patent is extended or adjusted under 35 U.S.C. 154(b) by 0 days.

(21) Appl. No.: 15/771,017

(22) PCT Filed: Oct. 18, 2016

(86) PCT No.: PCT/IB2016/056255
§ 371 (c)(1),
(2) Date: Apr. 25, 2018

(87) PCT Pub. No.: WO2017/077413
PCT Pub. Date: May 11, 2017

(65) Prior Publication Data
US 2018/0327431 A1  Nov. 15, 2018

(30) Foreign Application Priority Data

Nov. 6, 2015  (GB) .................................. 1519598.5

(51) Int. Cl.
| | |
|---|---|
| *B01J 23/72* | (2006.01) |
| *C07F 7/02* | (2006.01) |
| *B01J 37/04* | (2006.01) |
| *B01J 35/00* | (2006.01) |
| *B01J 21/06* | (2006.01) |

(52) U.S. Cl.
CPC ............... *C07F 7/025* (2013.01); *B01J 21/06* (2013.01); *B01J 23/72* (2013.01); *B01J 35/0006* (2013.01); *B01J 37/04* (2013.01)

(58) Field of Classification Search
None
See application file for complete search history.

(56) References Cited

U.S. PATENT DOCUMENTS 7,429,672 B2 * 9/2008 Lewis ...................... C07F 7/025
556/470

FOREIGN PATENT DOCUMENTS

| JP | 05170773 A | * | 7/1993 |
| JP | H05-170773 A | | 7/1993 |
| JP | H06-65257 A | | 3/1994 |
| JP | 2001-178018 A | | 6/2001 |

OTHER PUBLICATIONS

Suzuki et al: "Direct synthesis of trimethoxilisane from methanol and hydrogen-treated silicon using copper (II) chloride as a catalyst",Bull. Chem. Soc. Jpn, vol. 64, Jan. 1, 1991, pp. 3445-3447. (Year: 1991).*
Machine Translated version of Mitsuharu, JP-0517073-A. (Year: 1993).*
M Itsuharu et al., JP05170773A, Machine Translation (Year: 1993).*
Suzuki E. et al.: "Direct synthesis of trimethoxilisane from methanol and hydrogen-treated silicon using copper (II) chloride as a catalyst", Bulletin of the Chemical Society of Japan, Chemical Society of Japan, Tokyo, JP, vol. 64, 1991, pp. 3445-3447, XP007905936, ISSN: 0009-2673, DOI: 10.1246/BCSJ.64.3445, A method for the selective synthesis of SiH(OMe)3.
International Search Report for PCT/IB2016/056255, ISA/EP, Rijswijk, NL, dated Jan. 17, 0217.
Written Opinion of the ISA for PCT/IB2016/056255, ISA/EP, Rijswijk, NL, dated Jan. 17, 0217.

* cited by examiner

*Primary Examiner* — Clinton A Brooks
*Assistant Examiner* — Kofi Adzamli
(74) *Attorney, Agent, or Firm* — Harness, Dickey & Pierce, P.L.C.

(57) ABSTRACT

The invention provides a direct solvent free method for the selective synthesis of trialkoxysilanes having the formula $SiH(OR)_3$, the method comprises providing a mixture of metallic silicon and copper based catalyst in a packed bed reactor, wherein neither the metallic silicon nor the silicon-catalyst mixture is subjected to any washing step. Claim 1 relates to a direct solvent free method for the selective synthesis of trialkoxysilanes having the formula $SiH(OR)_3$, wherein each R is a $C_1$-$C_4$ alkyl, the method comprising the steps of: providing a mixture of metallic silicon and copper based catalyst in a packed bed reactor; heating the mixture at an activation temperature of about 180° C.-about 250° C.; introducing $C_1$-$C_4$ alcohol to the reactor at a reaction temperature of about 180° C.-less than about 250° C.; condensing the reaction products in a heat exchanger; and collecting the condensed reaction products, wherein neither the metallic silicon nor the silicon-catalyst mixture is subjected to any washing step, including a hydro fluoric acid (HF) washing step.

13 Claims, 5 Drawing Sheets

METHOD FOR THE SELECTIVE SYNTHESIS OF TRIALKOXYSILANES

CROSS-REFERENCE TO RELATED APPLICATIONS

This application is a 371 U.S. National Stage of International Application No. PCT/162016/056255, filed Oct. 18, 2016, which claims the benefit of and priority to British Patent Application No. 1519598.5, filed Nov. 6, 2015. The entire disclosures of the above applications are incorporated herein by reference.

INTRODUCTION

This invention relates to a direct method for the synthesis of trialkoxysilanes. In particular, but not exclusively, this method relates to a method for the selective synthesis of triethoxysilane.

BACKGROUND

Trialkoxysilanes undergo various reactions such as addition, co-polymerization, co-polycondensation and disproportionation with other organic compounds to form organo-silicon compounds.

The disproportionation reaction leads to formation of silane, which is a precursor for solar-grade silicon production. The widely used method for the synthesis of alkoxysilanes involves the reaction of silicon with hydrochloric acid to form trichlorosilane (Equation 1) which is then reacted with primary alcohols in the presence of a copper catalyst (Equation 2).

$$Si + 3HCl \rightarrow SiHCl_3 + H_2 \quad (1)$$

$$SiHCl_3 + 3ROH \rightarrow SiH(OR)_3 + 3HCl \quad (2)$$

However, this approach is faced with challenges including the poor conversion of silicon, low selectivity and poor yield of the desired trialkoxysilane product in addition to the toxic and corrosive hydrochloric acid by-product.

Therefore, much attention has been paid to the development of a direct synthesis method (Equation 3), and the improvement of the selectivity for the trialkoxysilane.

$$Si + 3ROH \rightarrow SiH(OR)_3 + H_2 \quad (3)$$

The direct synthesis method has to date been carried out in continuously stirred slurry phase tank reactors using heat transfer solvents, such as diphenylalkanes. The use of heat transfer solvents result in prolonged catalyst activation time and also complicate the purification process. This slurry phase method also suffers from low selectivity and yield of the desired trialkoxysilane product, as well as the slow conversion of metallic silicon.

JP2001-178018 describes a production process for polycrystalline silicon and high purity silicon. However, the method described for the production of trialkoxysilane takes place in a fluidized bed reactor, and according to the examples provided, in the presence of a catalyst containing Cu, Al, and Fe. According to the description the method achieves selectivity for trimethoxysilane of about 75%. Such a low selectivity for the desired product may be problematic for a number of reasons, including the associated negative cost implication, and the need for additional separation steps in the process.

Accordingly there is a need for an alternative method for the synthesis of trialkoxysilanes that addresses the above-mentioned shortcomings.

SUMMARY OF THE INVENTION

According to a first aspect to the present invention there is provided a direct solvent free method for the selective synthesis of trialkoxysilanes having the formula $SiH(OR)_3$, wherein each R is a $C_1$-$C_4$ alkyl, the method comprising the steps of:
  providing a mixture of metallic silicon and copper based catalyst in a packed bed reactor;
  heating the mixture at an activation temperature of about 180° C.-about 250° C.;
  introducing $C_1$-$C_4$ alcohol to the reactor at a reaction temperature of about 180° C.-less than about 250° C.;
  condensing the reaction products in a heat exchanger; and
  collecting the condensed reaction products,
wherein neither the metallic silicon nor the silicon-catalyst mixture is subjected to any washing step, including a hydrofluoric acid (HF) washing step.

In a preferred embodiment the method has a selectivity for trialkoxysilane of greater than about 88%, greater than about 90%, or greater than about 95%. In one embodiment the $C_1$-$C_4$ alcohol is a primary alcohol.

In one embodiment the $C_1$-$C_4$ alcohol has a residence time of about 9 minutes to about 71 minutes in the reactor.

In one embodiment the copper based catalyst is present at a catalyst loading concentration of about 2 wt. % to about 10 wt. % by weight of the silicon-catalyst mixture.

In a preferred embodiment the copper based catalyst is present at a catalyst loading of less than about 5 wt. % by weight of the silicon-catalyst mixture.

In a particularly preferred embodiment the copper based catalyst is present at a catalyst loading of about 2.5 wt. % by weight of the silicon-catalyst mixture.

Preferably, the copper based catalyst is selected from the group consisting of copper (I) chloride, copper (II) hydroxide, copper (II) oxide, and mixtures thereof.

In one embodiment the $C_1$-$C_4$ alcohol is substantially anhydrous.

Preferably, the $C_1$-$C_4$ alcohol is ethanol.

In one embodiment the activation temperature is about 220° C.

In a preferred embodiment the packed bed reactor is heated at an activation temperature of about 220° C. for a period of about 2-5 hours.

In a further preferred embodiment the reaction temperature is about 200° C.-about 240° C.

Preferably, the reaction temperature is about 220° C.

More preferably, the reaction temperature is about 240° C.

In one embodiment the residence time is about 14 minutes to about 71 minutes.

According to a second aspect to the present invention there is provided a solvent free method for the synthesis of triethoxysilane, the method having a selectivity for triethoxysilane of greater than about 90%, the method comprising the steps of:
  providing a mixture of metallic silicon and copper based catalyst in a packed bed reactor at a catalyst loading of less than about 5 wt. % by weight of the silicon-catalyst mixture;
  heating the mixture at an activation temperature of about 220° C.;
  introducing anhydrous ethanol to the reactor such that the ethanol has a residence time of about 35 minutes to about 71 minutes in the reactor, at a reaction temperature of about 220° C.-about 240° C.;
  condensing the reaction products in a heat exchanger; and
  collecting the condensed reaction products, wherein neither the metallic silicon nor the silicon-catalyst mixture is subjected to any washing step, including a HF washing step.

BRIEF DESCRIPTION OF THE DRAWINGS

The invention will now be described in more detail with reference to the following non-limiting embodiments and figures in which.

DETAILED DESCRIPTION OF A PREFERRED EMBODIMENT

The present invention will now be described more fully hereinafter with reference to the accompanying figures, in which some of the non-limiting embodiments of the invention are shown.

The invention as described hereinafter should not be construed to be limited to the specific embodiments disclosed, with slight modifications and other embodiments intended to be included within the scope of the invention.

Although specific terms are employed herein, they are used in a generic and descriptive sense only and not for purposes of limitation.

As used herein, throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having", "including", and variations thereof used herein, are meant to encompass the items listed thereafter, and equivalents thereof as well as additional items.

As used herein, the term "direct method" should be understood to mean the formation of the trialkoxysilane by the reaction of silicon and an alcohol without passing through an intermediate. (Some prior arts first react silicon with HCl to form the intermediate $SiHCl_3$ which then reacts with an alcohol to form the trialkoxysilane).

As used herein, the term "solvent free" should be understood to mean a reaction or method wherein the reagents are not suspended or dissolved in a solvent or a vehicle that is not a reagent in the particular reaction. As used in this specification the terms "solvent free" and "non-slurry" has the same meaning.

As used herein, the term "selective synthesis" refers to a preference for the trialkoxysilane reaction product over any other product formed in the reaction, including tetraalkoxysilane, of greater than 80 wt. %, preferably greater than 90 wt. %, even more preferably greater than 95 wt. %.

As used herein, the term "copper based catalyst" refers to a catalyst consisting of substantially pure copper based compounds, including copper (I) chloride, copper (II) hydroxide, copper (II) oxide, and mixtures thereof. The term "substantially pure" should be understood to mean a purity of greater than 98%, greater than 99.0, or greater than 99.5%.

As used herein, the term "semi-continuous" should be understood to mean that one of the reagents (alcohol) and all products (unreacted alcohol and alkoxysilanes) are simultaneously charged and discharged from the reactor respectively whilst the other reagent (silicon) is stationary in the reactor. It is envisaged that the method according to the present invention may be semi-continuous or continuous.

The present invention provides for a direct solvent free method for the selective synthesis of trialkoxysilanes having the formula $SiH(OR)_3$. Each R is a $C_1$-$C_4$ alkyl.

The direct method comprises reacting elemental silicon with primary alcohols in a packed tubular reactor in the presence of a copper based catalyst. The method is a solvent free (non-slurry) method which may be semi-continuous or continuous.

Figure 1:
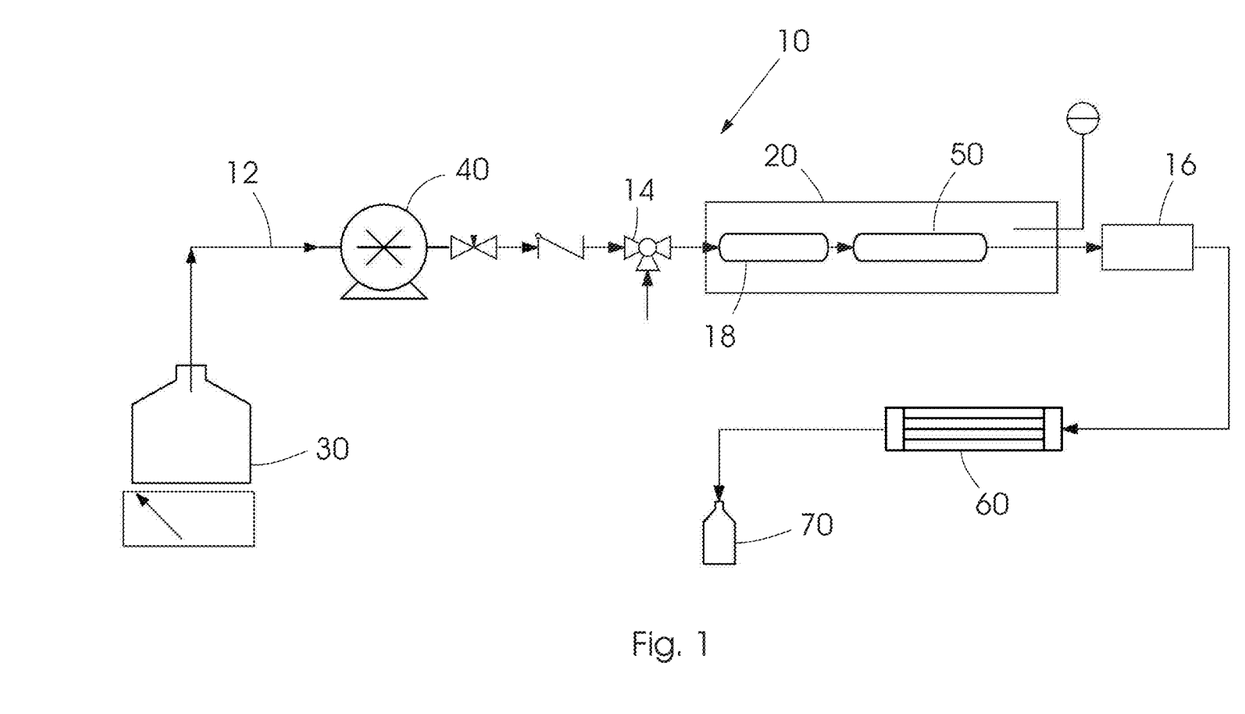
FIG. 1 shows a schematic representation of the tubular reactor system used in the method according to the present invention.

FIG. 1 shows a schematic representation of the reactor system 10 that can be used in the method of the present invention. The reactor system 10 comprises an alcohol reservoir 30, a pump 40, a tubular reactor 50 within the tubular furnace 20, a condenser 60, and a reservoir 70 for collecting the reaction products. Alcohol from the reservoir 30 is pumped to the tubular reactor via a feed line 12. The reactor system 10 may further comprise a nitrogen inlet 14 for purging the catalyst silicon mixture in the tubular reactor during an activation cycle. The reactor system 10 may also comprise a back pressure regulator 16 and a pre-vaporisation column 18, which column is positioned in the tubular furnace 20.

The tubular furnace 20 is used to heat the catalyst silicon mixture to an activation temperature, and to keep the mixture at this activation temperature for a set amount of time. After the catalyst silicon mixture has gone through the activation cycle, the temperature of the tubular furnace 20 may be adjusted to the reaction temperature.

It will be appreciated by those skilled in the art the reactor system 10 described above is a representation of one example of a system that may be used in the method of the present invention. The reactor system may be designed to include a plurality of primary alcohol reservoirs, pumps, tubular reactors, furnaces, and condensers. For example, the reactor system may be designed to include a plurality of packed tubular reactors that are cycled and recharged with a silicon catalyst mixture in order to make the process continuous. The system may also be monitored and adjusted electronically according to methods known in the art.

The tubular reactor 50 is packed with a mixture of powdered metallic silicon and copper based catalyst, and then plugged at both ends thereof to prevent catalyst or silicon carry over. The copper based catalyst may be mixed with the silicon at a catalyst loading concentration of about 2 wt. % to about 10 wt. % by weight of the silicon-catalyst mixture. Preferably the copper based catalyst is present in the mixture at a concentration of less than about 5 wt. %. Most preferably, the copper based catalyst is present in the mixture at a concentration of 2.5 wt. %. Furthermore, the copper based catalyst is a substantially pure compound, or mixture of compounds, that does not contain any significant levels of impurities, such as aluminium or iron, that may impact negatively on the selectivity of the process.

The method according to the present invention does not include any additional steps to prepare, activate or clean the metallic silicon, the copper based catalyst, or the silicon-catalyst mixture. In particular, the method does not require or include the step of washing the metallic silicon, the copper based catalyst, or the silicon-catalyst mixture with any acid or other preparatory solution such as hydrofluoric acid (HF). HF is known to be an extremely corrosive liquid and it is also considered a contact poison. The use of HF in a chemical process poses great health risks. Owing to its low acid dissociation constant, HF as a neutral lipid-soluble molecule that penetrates tissue more rapidly than typical mineral acids. Because of the ability of hydrofluoric acid to penetrate tissue, poisoning can occur readily through exposure of skin or eyes, or when inhaled or swallowed. Accordingly, it is desirable to exclude HF from any chemical processing system where possible.

The packed tubular reactor is then connected with the feed line 12 and placed within the tubular furnace. The tubular furnace may also comprise a pre-vaporisation column 18 which is packed with silicon carbide and molecular sieves. The pre-vaporization column may also be packed with similar materials, including other ceramic or refractory or any other materials that do not react with alcohol or are chemically inert and resistant to high temperatures, for example tungsten carbide, molybdenum, aluminium oxide, magnesium oxide, calcium oxide, tantalum, and rhenium. Preferably the material should be cheap. Without thereby wishing to be bound by any particular theory, it is believed that the pre-vaporization column acts to convert liquid alcohol to vapour phase before reaching the silicon in the reactor. If the alcohol is not pre-vapourized, some of it may not sufficiently react thereby contributing to low silicon conversion. It is essential that the pre-vapourization column should be packed with an inert and high temperature resistant material. The packing assists in making sure that the alcohol is uniformly vapourized. The packing also assists in removing any residual water from the alcohol in the case where the packing is molecular sieves or a mixture of molecular sieves and silicon carbide.

A packed bed reactor, used in gas-solid reactions, consists of a compact immobilized stack of a catalyst or reactant within a vertical or horizontal vessel into which vaporized reagents are added for the reaction to occur on the bed and products are continuously removed. In this reactor the solid can either be a reactant or a catalyst. The catalyst or the solid reactant is held in the reactor and does not need to be separated from products.[1] Industrial packed bed reactors range in size from small diameter to large diameter packed beds and are smaller than fluidized bed reactors.

Packed bed reactors offer advantages of ideal plug flow behaviour, lower maintenance, operation and construction costs and reduced loss due to attrition and wear. The other advantage is that there is more contact between reactant and catalyst than in other types of reactors and this lead to increased product formation and selectivity due to high conversion rate per weight of catalyst.[2] Packed bed reactors are continuously operated and are effective at high temperatures and pressures. The use of heterogeneous catalysts, which can be regenerated, means that the process is less costly and environmentally friendly. In situ activation of the catalyst ensures that the catalyst is freshly prepared before the reaction. Packed bed reactors also offer the advantage of continuous flow production and lead to high throughput.[3]

Large packed bed reactors are characterized with difficult temperature control and consequently poor heat transfer may also result in the generation of hot spots and thermal degradation of the catalyst. Channeling of the gas stream can occur, leading to ineffective regions in the reactor and side reactions are possible. The replacement of catalyst or solid reactant is also difficult in fixed-bed reactors and may require shutting down the process. Another major disadvantage of packed bed reactor is plugging of the bed, due to coke deposition which results in high pressure drop.[4]

On the other hand, a fluidized bed reactor consists of a bed of granular solid material, supported over a fluid distributing plate and is made to behave like a liquid by the passage of fluid which could be gas or liquid at a flow rate above a certain critical value. This type of reactor is useful in carrying out several multiphase reactions.[5] Fluidized bed reactors are nowadays used in a vast number of industrial applications, which encompass the chemical, metallurgical, environmental and pharmaceutical sector. The most important advantage of fluidized reactors arises from the fact that the solid materials it contains are in a continuous motion and are normally well mixed. This leads to rapid elimination of hot spots and the bed works essentially in an isothermal manner. Particle motion in this type of reactor makes temperature control easy because of the very high bed-to-surface heat.[6] The fluid-like properties of the gas-solid mixture enable the solid to be transferred without difficulty from one reaction vessel to another and this is a useful feature that allows continuous flow synthesis coupled with high throughput. Fluidized bed reactors have low maintenance costs since they have no moving parts and are not mechanically agitated.

The disadvantages of fluidized beds include the erosion of internal components caused by the fluid-like behaviour of fine solid particles within the bed and loss of fine particles through cyclone plugging, which can be costly if the catalyst or the starting material is expensive. There could also be the by-passing of the solid by gas bubbles which could severely limit conversion. Reactions that require a temperature gradient inside the reactor cannot be accomplished in a fluidized reactor.[7] Another disadvantage is that fine-sized particles need special techniques for fluidization. The fluidized reactor can result in undesirable products and complicated separation techniques as a result of generation of fines due to turbulent mixing, gas or liquid gas interaction at the distributor site and segregation due to agglomeration. The fact that the bed material in the reactor is expanded means that large vessels are needed for construction of fluidized reactors as compared to packed bed reactors. This is a disadvantage in terms of space and initial costs. This type of reactor can also be expensive in terms of energy needed for pumping in order to maintain fluidity. Pressure drops often occur and this leads to loss of bed surface area leading to low conversions.[8]

The catalyst-silicon mixture in the packed tubular reactor is activated by heating the mixture in an activation cycle to an activation temperature of about 180° C. to about 250° C. for a period of about 2 to 5 hours, while purging the system with nitrogen, or any other inert gas at a suitable flow rate. Preferably the activation temperature is below 240° C. Most preferably the activation temperature is 220° C., and the activation cycle is about 2.5 hours. The method according to the present invention offers relatively short in situ catalyst activation time since it does not use heat transfer solvents as used in the slurry phase reactions of the prior art. Once the activation cycle has been completed the temperature of the system may be altered, up or down as the case may be, to the reaction temperature. The reaction temperature of the system may be in the range of about 180° C. to less than about 250° C. Preferably the reaction temperature is in the range of about 220° C. to about 240° C. Most preferably the reaction temperature is about 220° C.

It will be appreciated by those skilled in the art of chemical processing that even minor reductions in reaction temperatures employed in reactor systems could lead to drastic energy and therefore cost savings. Therefore, it will be appreciated that it is a significant advantage to be able to obtain the same or comparable product selectivity, rate of product formation, and rate of reagent conversion at a temperature of about 220° C., compared to a temperature of about 250° C., for example.

The alcohol is pumped from the reservoir 30 via the feed line 12 to the pre-vaporisation column 18 and the tubular reactor 50 which are housed within the tubular furnace 20. The flow rate of the alcohol may be selected in the range of about 0.1 to about 0.8 mL/min. Preferably the flow rate is selected in the range of about 0.1 to about 0.3 ml/min. Most preferably the flow rate is about 0.1 mL/min or 0.2 mL/min. Based on the design and volume of the reactor used, the flow rates equate to a residence time in the range of about 9 minutes to about 71 minutes. Preferably the residence time is in the range of about 24 minutes to about 71 minutes. Most preferably the residence time is in the range of about 35 minutes to about 71 minutes. The pump 40 may be a pump typically used in a high pressure liquid chromatography (HPLC) system, or any other pump that can deliver an accurate of flow rate in the range of about 0.1 to about 0.8 mL/min, or depending on the volume of the reactor, a pump that can produce a residence time of about 9 minutes to about 71 minutes.

The alcohol used in the method according to the present invention is preferably anhydrous alcohol which is optionally stored on molecular sieves within the reservoir 30. The reaction products formed in the tubular reactor and the excess unreacted alcohol then passes to a condenser where the products are condensed. Without thereby wishing to be bound by any particular theory, it is believed that water contained within the alcohol poison the catalyst and reduce trialkoxysilane selectivity and conversion of silicon. It may also react with the formed alkoxysilanes to form silica sol or siloxanes leading to loss of products. The method of the present invention produces trialkoxysilanes in high selectivity with an acceptable rate of formation and silicon conversion percentage.

Several experiments were conducted to evaluate each parameter of the reaction, and how it affects selectivity, rate of formation, and/or rate of silicon conversion. The method according to the present invention will now be more fully discussed according to the experiments, results and data provided below.

EXPERIMENTS—TYPICAL PROCEDURE

Powdered metallic silicon (99.0%, <325 μm) 5.2651 g and copper based catalyst (<250 μm) 0.2522 g were mixed thoroughly and packed into an already assembled stainless steel tubular reactor (150 mm×9.925 mm).

The reactor was plugged at both ends by the use of glass wool to prevent any catalyst or silicon carry over. The reactor was connected to the reactor system and placed horizontally in the middle of a tubular furnace which was plugged with glass wool at both outlets to minimize heat loss.

A pre-vaporization column (150 mm×9.925 mm), packed with silicon carbide and molecular sieves, was connected before the reactor. For some of the experiments, a back pressure regulator (0 to 34.4 bar) was connected after the column.

The condenser and the pump which fed water to the heat exchanger were switched on. The silicon-catalyst mixture was heated to the activation temperature for a period of 2.5 to 5 hours while the system was purged with nitrogen at a flow rate of 40 mL/min. The temperature was then adjusted to the reaction temperature and anhydrous ethanol stored in molecular sieves was then metered into the reactor using an HPLC pump at the selected flow rate. The formed reaction products and excess ethanol (distillates) were condensed in the condenser and were collected for gas chromatography (GC) analysis at 1 h intervals.

The flow rates selected were in the range of 0.1 to 0.8 mL/min. Therefore, based on the dimensions of the reactor, the selected flow rates equate to a residence time range of 9 minutes to 71 minutes. It will be appreciated by those skilled in the art that the flow rate may be altered according to the reactor design to achieve a residence time in the range indicated above.

Experiment 1: The Effect of Copper Catalyst Type on the Rate of Triethoxysilane Formation The effect of copper catalyst type on the rate of triethoxysilane formation was investigated for copper (I) chloride, copper (II) hydroxide, copper (II) oxide, and copper (II) sulphate. A control experiment was conducted with no catalyst present.

The reaction was carried out using the typical procedure as described above. The specific reaction conditions employed were: mass of silicon 5 g, flow rate 0.1 mL/min, activation time 2.5 hours, catalyst loading 5 wt. %, reaction temperature 240° C., activation temperature 220° C.

Figure 2:
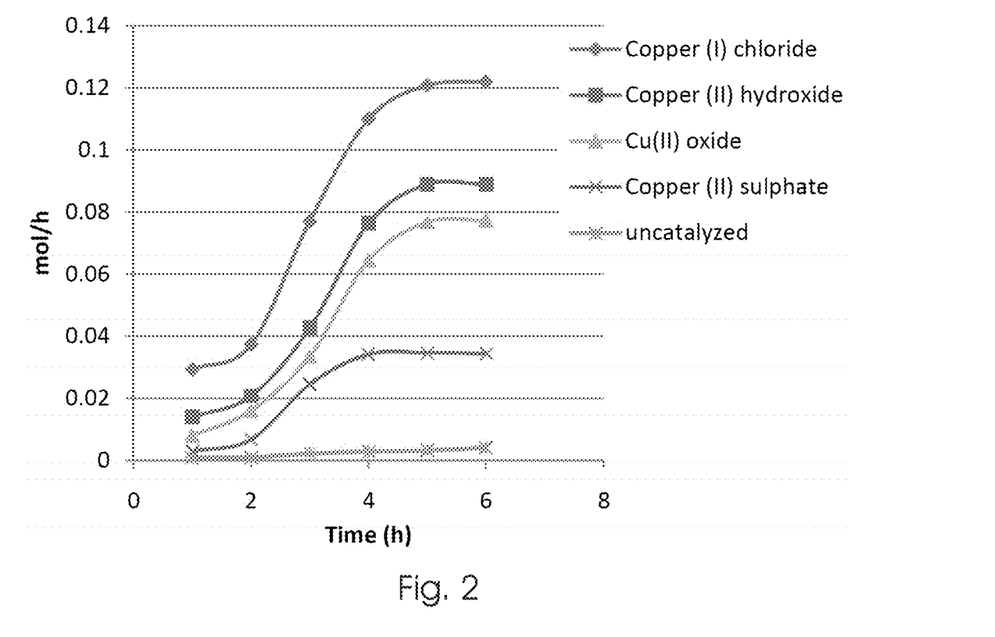
FIG. 2 shows a graphical representation of the effect of the copper catalyst type on the rate of triethoxysilane formation.

FIG. 2 shows a graphical representation of the results obtained for the above experiment. As can be seen from FIG. 2, copper (I) chloride, copper (II) hydroxide, copper (II) oxide shows similar reaction rate profiles, with copper (I) chloride being preferred over copper (II) hydroxide and copper (II) oxide. Although the copper (II) sulphate catalysed reaction did yield triethoxysilane, the rate of the reaction not ideal. The rate of triethoxysilane formation was negligible for the uncatalysed reaction.

Experiment 2: The Effect of Catalyst Loading on the Rate of Triethoxysilane Formation The effect of catalyst loading concentration on the rate of triethoxysilane formation was investigated for catalyst loading concentrations of 2.5 wt. %, 5 wt. %, 10 wt. %, and 15 wt. %. A control experiment as conducted with no catalyst present.

The reaction was carried out using the typical procedure as described above. The specific reaction conditions employed were: mass of silicon 5 g, flow rate 0.1 mL/min, activation time 2.5 hours, catalyst loading 5 wt. % CuCl, reaction temperature 240° C., activation temperature 220° C.

Figure 3:
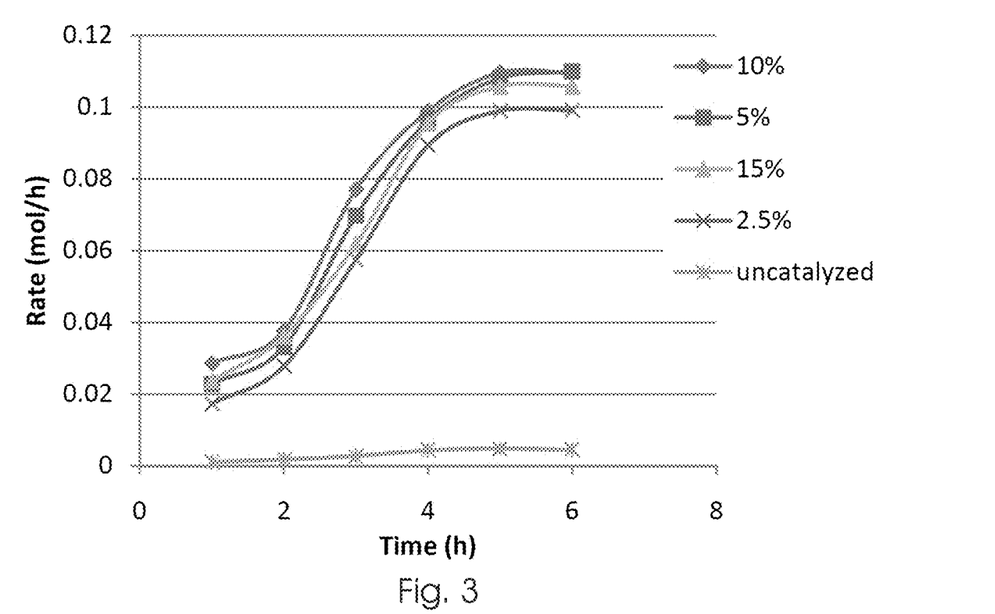
FIG. 3 shows a graphical representation of the effect of the copper catalyst loading on the rate of triethoxysilane formation.

FIG. 3 shows graphical representation of the results obtained for the above experiment. As can be seen from FIG. 3, comparable reaction rates were obtained for all the selected catalyst loading concentrations. The rate of triethoxysilane formation was negligible for the uncatalysed reaction.

The results obtained in this experiment confirms that a catalyst loading concentration of 2.5 wt. % by weight of the catalyst-silicon mixture is substantially equally as effective compared to higher loadings, for the method according to the present invention.

Experiment 3: The Effect of Activation Temperature and Activation Time on the Rate of Triethoxysilane Formation The effect of activation temperature on the rate of triethoxysilane formation was investigated for 220° C., 350° C., 500° C., and 700° C. A control experiment was conducted with no catalyst present. Further, the effect of the duration of the activation cycle on the rate of triethoxysilane formation was investigated for 2.5, 5, 15 and 20 hours.

The reaction was carried out using the typical procedure as described above. The specific reaction conditions employed for the temperature experiments were: mass of silicon 5 g, flow rate 0.1 mL/min, activation time 2.5 hours, catalyst loading 5 wt. % CuCl, reaction temperature 240° C. The specific reaction conditions employed for the activation time experiments were: mass of silicon 5 g, flow rate 0.1 mL/min, catalyst loading 5 wt. % CuCl, reaction temperature 240° C., and activation temperature 220° C.

Figure 4:
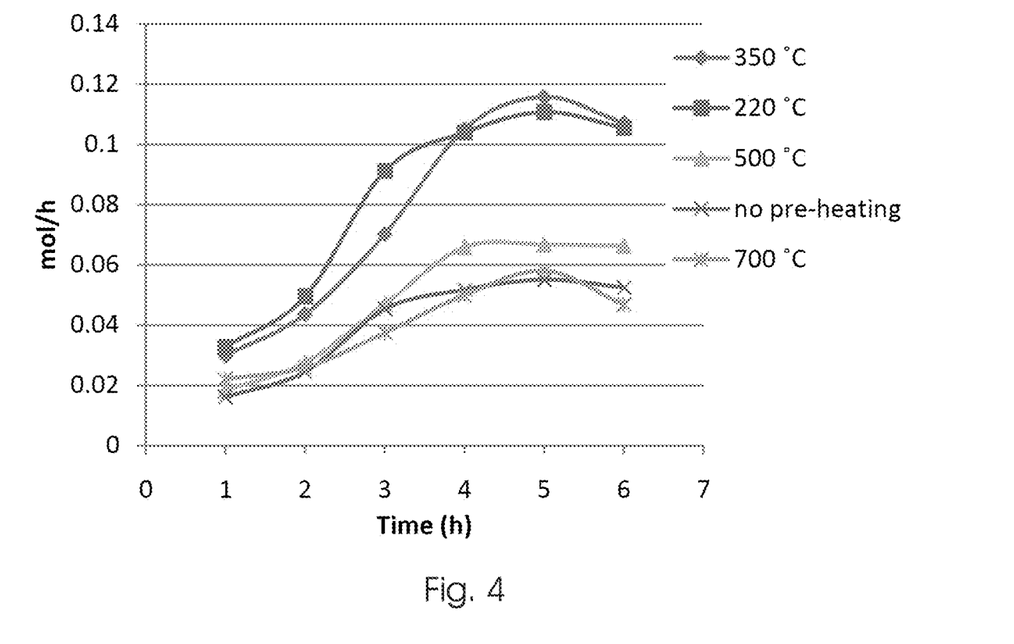
FIG. 4 shows a graphical representation of the effect of activation temperature on the rate of triethoxysilane formation.

FIG. 4 shows a graphical representation of the results obtained for the activation temperature experiments. As can be seen from FIG. 4, an activation temperature of 220° C. proved to be substantially as effective as an activation temperature of 350° C. It appears that the catalyst deactivated to an extent when the activation temperature was over 500° C., as the rate of triethoxysilane formation for the 500° C. and 700° C. experiments were similar compared to the rate of formation where no activation cycle was used. It is clear from this experiment that an activation temperature of 220° C., or perhaps even less, may be employed in the method according to the present invention.

Figure 5:
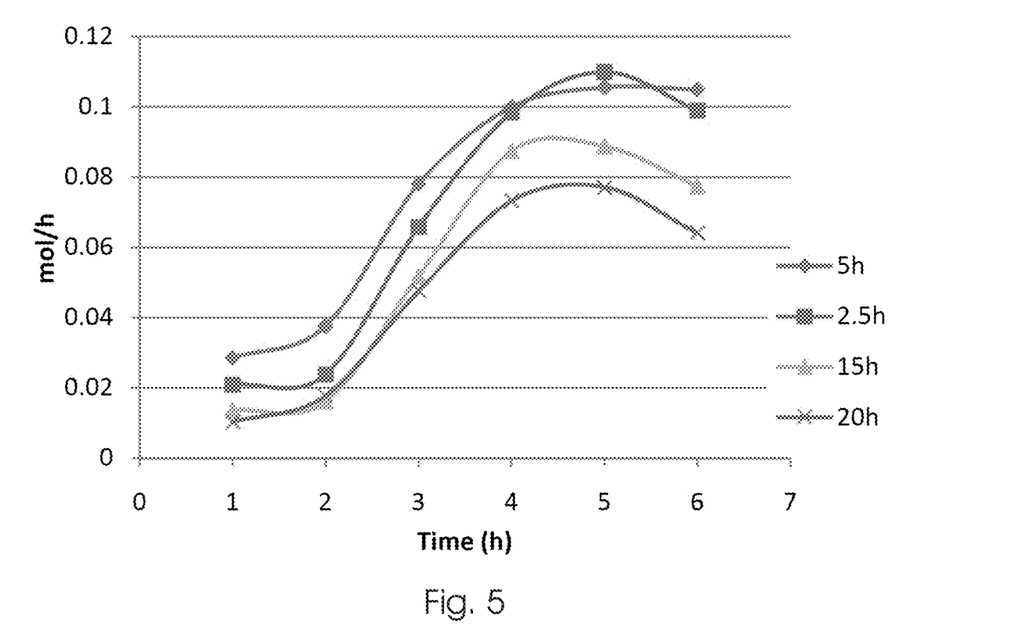
FIG. 5 shows a graphical representation of the effect of activation time on the rate of triethoxysilane formation.

FIG. 5 shows a graphical representation of the results obtained for the activation time experiments. As can be seen from FIG. 5, the results seem to indicate that an optimal activation cycle may be one that is in the region of 2.5 to 5 hours. Where the activation cycle is too long, i.e. greater than 15 hours, the rate of triethoxysilane formation goes down.

Experiment 4: The Effect of Reaction Temperature on TES Selectivity and Silicon Conversion The effect of reaction temperature on silicon conversion and selectivity for triethoxysilane (TES) was investigated after 24 hours and 6 hours respectively.

The reaction was carried out using the typical procedure as described above. The specific reaction conditions employed were: mass of silicon 5 g, flow rate 0.1 ml/min, activation time 2.5 hours, catalyst loading 5 wt. % CuCl, reaction temperature 180° C.-220° C., activation time 2.5 hours.

As can be seen from the results presented in Table 1 presented below, reaction temperatures of 220° C. and 240° C. were more effective in terms of both selectivity and conversion when compared to a reaction temperature of 180° C. However, it was noted that both selectivity and conversion rates decreases when the temperature was higher than 240° C.

TABLE 1

Effect of reaction temperature on silicon conversion and TES selectivity.

| Reaction Temp. (° C.) | TES selectivity after 6 h (%) | Si conversion after 24 h (%) |
|---|---|---|
| 180 | 80.6 | 54.5 |
| 200 | 86.2 | 59.2 |
| 220 | 93.8 | 62.9 |
| 240 | 95.5 | 64.8 |
| 260 | 94.1 | 63.3 |

Figure 6:
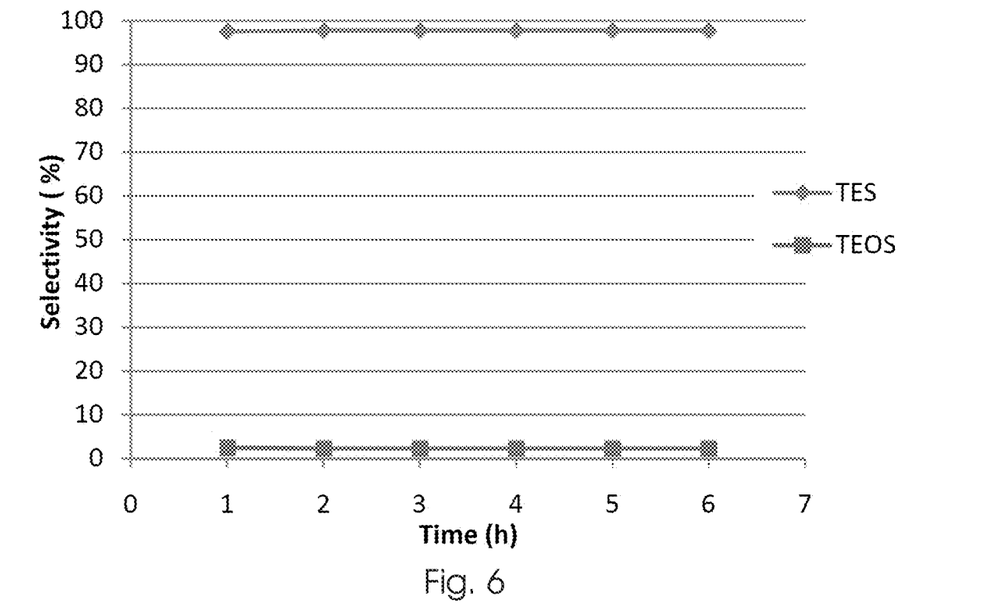
FIG. 6 shows a graphical representation of the selectivity of TES and TEOS over time.
Figure 7:
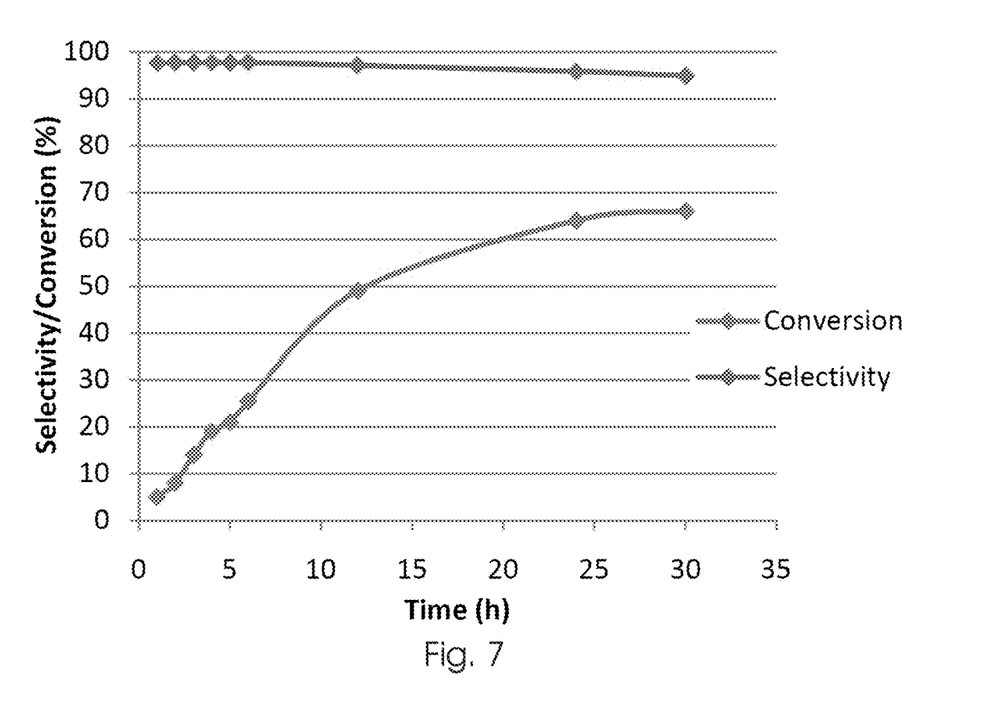
FIG. 7 shows a graphical representation of the silicon conversion and triethoxysilane selectivity over 30 hours.

Further to the above, FIG. 6 shows a graphical representation of the selectivity for TES over tetraethoxysilane (TEOS) at 240° C. over a period of 6 hours, while FIG. 7 shows a graphical representation of silicon conversion and TES selectivity over a period of 30 hours at a reaction temperature of 240° C.

Experiment 5: The Effect of Flow Rate on TES Selectivity and Silicon Conversion

The effect of flow rate on TES selectivity and silicon conversion was investigated at 6 hours and at 24 hours.

The reaction was carried out using the typical procedure as described above. The specific reaction conditions employed were: mass of silicon 5 g, flow rate 0.1-0.8 mL/min, activation time 2.5 hours, catalyst loading 5 wt. % CuCl, reaction temperature 240° C., activation temperature 220° C.

It is clear from the results presented in Table 2 presented below that flow rates of 0.1-0.3 mL/min are optimal for TES selectivity, although 0.5 mL/min and 0.8 mL/min may also be employed to satisfactory effect.

TABLE 2

Effect of flow rate on TES selectivity

| Ethanol flow rate (mL/min) | TES selectivity after 6 h (%) | TES selectivity after 24 h (%) |
|---|---|---|
| 0.1 | 97.11 | 94.76 |
| 0.2 | 96.78 | 93.49 |
| 0.3 | 95.62 | 92.31 |
| 0.5 | 91.6 | 89.32 |
| 0.8 | 86.4 | 82.43 |

As seen for TES selectivity, it can be seen from the results presented in Table 3 below that flow rates of 0.1-0.3 mL/min are also preferred when the reaction is considered based on silicon conversion. However, flow rates of 0.5 mL/min and 0.8 mL/min may also be employed to satisfactory effect.

TABLE 3

Effect of flow rate on silicon conversion.

| Ethanol flow rate (mL/min) | Si conversion after 6 h (%) | Si conversion after 24 h (%) |
|---|---|---|
| 0.1 | 25.03 | 64.3 |
| 0.2 | 24.77 | 62.1 |
| 0.3 | 23.31 | 59.8 |
| 0.5 | 20.27 | 53.8 |
| 0.8 | 18.47 | 51.5 |

EXPERIMENTS—OTHER DATA

In another experiment that was conducted the selectivity for TES over TEOS was followed over a period of 6 hours.

The reaction was carried out using the typical procedure as described above. The specific reaction conditions employed were: mass of silicon 5 g, flow rate 0.1 mL/min, activation time 2.5 hours, catalyst loading 5 wt. % CuCl, reaction temperature 240° C., activation temperature 220° C.

As can be seen from the data provided in Table 4 below, the method according to the present invention produces trialkoxysilanes in high selectivity (>95 wt. %). Further as was shown above, the reactions proceed with an acceptable rate of formation and silicon conversion percentage.

TABLE 4

Mass of ethanol used, mass of fractions collected per hour and % composition of silicon containing products.

| Reaction time (h) | Mass of ethanol used | Mass of fractions collected | % TES | % TEOS |
| --- | --- | --- | --- | --- |
| 1 | 4.4 | 3.4 | 97.6 | 2.4 |
| 2 | 4.5 | 3.5 | 97.701 | 2.299 |
| 3 | 4.6 | 3.7 | 97.705 | 2.295 |
| 4 | 4.5 | 3.6 | 97.707 | 2.293 |
| 5 | 4.3 | 3.7 | 97.709 | 2.291 |
| 6 | 4.7 | 3.8 | 97.722 | 2.287 |

In other experiments that were conducted the effect of the R-group of the primary alcohol on silicon conversion and TES selectivity were investigated and compared for methanol, ethanol, n-propanol, and n-butanol at 6 hours and at 24 hours.

The reaction was carried out using the typical procedure as described above. The specific reaction conditions employed were: mass of silicon 5 g, flow rate 0.1 mL/min, activation time 2.5 hours, catalyst loading 5 wt. % CuCl, reaction temperature 240° C., activation temperature 220° C.

Figure 8:
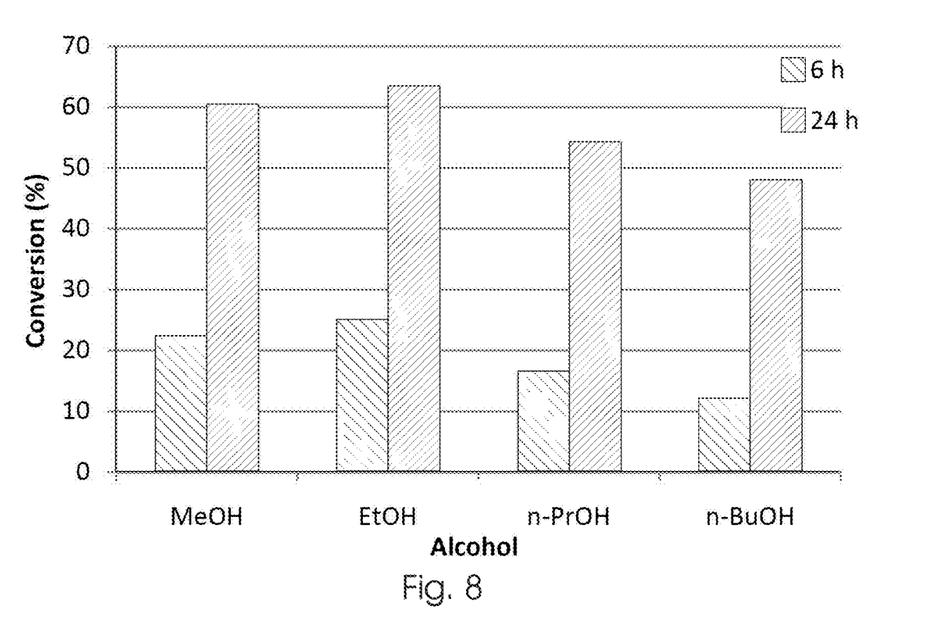
FIG. 8 shows a graphical representation of the silicon conversion rate for methanol, ethanol, n-propanol, and n-butanol at 6 hours and 24 hours.

FIG. 8 shows a graphical representation of the results obtained for the silicon conversion experiments at 6 hours and at 24 hours respectively. As can be seen from FIG. 8, silicon conversion rates were above 60 percent for methanol and ethanol (at 24 hours), while the conversion results for propanol and butanol are also considered acceptable.

Figure 9:
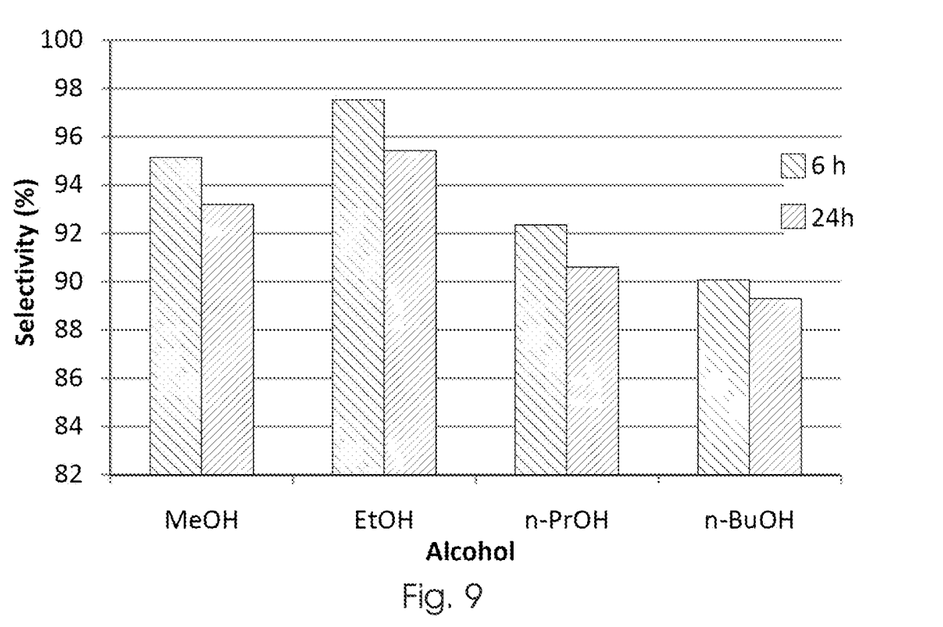
FIG. 9 shows a graphical representation of the selectivity for trialkoxysilane for methanol, ethanol, n-propanol, and n-butanol.

FIG. 9 shows a graphical representation of the results obtained for the trialkoxysilane selectivity (over tetraalkoxysilane) experiments at 6 hours and at 24 hours respectively. As can be seen from FIG. 9, selectivity percentages were above 94 percent for methanol and ethanol (at 6 hours), while the selectivity results for propanol and butanol were also extremely good at above 90 percent.

This above description and experiments are illustrative embodiments of the invention to indicate how the invention can be made and carried out. Those of ordinary skill in the art will know that various details may be modified thereby arriving at further embodiments, but that these embodiments will remain within the scope of the invention. For example, it will be appreciated that the reaction system itself may be considered modular and that various configurations may be employed, or the size and shape of the reactor, pre-vaporisation column, and furnace may be adjusted to suit operational needs.

REFERENCES

1. Poling B, Prausnitz J, O'Connell J. The Properties of gases and liquids. McGraw-Hill Companies Inc; 2001.
2. Jakobsen H A. Chemical reactor modelling: Multiphase reactive flows. 2nd Ed. Springer; 2014.
3. Doraiswamy L K, liner D. Chemical reaction engineering; Beyond the fundamentals. CRC Press; 2013.
4. Salmi T O, Mikkola J, Warna J P. Chemical reaction engineering and reactor technology. CRC Press; 2011
5. Yates J G. Fundamentals of fluidized-Bed chemical processes: Butterworths monographs in chemical engineering. Butterworth-Heinemann; 2013.
6. Gupta C K, Sathiyamoorthy D. Fluid bed technology in materials processing. CRC Press; 1998.
7. Kunii D, Levenspiel O. Fluidization engineering: Butterworth-Heinemann Series in Chemical Engineering. Butterworth-Heinemann; 1991.
8. Yang W. Handbook of fluidization and fluid-particle systems: Chemical Industries. CRC Press; 2003.

The invention claimed is:

1. A direct solvent free method for the selective synthesis of trialkoxysilanes having the formula $SiH(OR)_3$, wherein each R is a $C_1$-$C_4$ alkyl, the method comprising the steps of:
   providing a mixture of metallic silicon and copper based catalyst in a packed bed reactor, wherein the copper based catalyst is selected from the group consisting of copper (I) chloride, copper (II) hydroxide, copper (II) oxide, and mixtures thereof;
   heating the mixture at an activation temperature of about 180° C.-about 250° C.;
   introducing $C_1$-$C_4$ alcohol to the reactor at a reaction temperature of about 180° C.-less than about 250° C.;
   condensing the reaction products in a heat exchanger; and
   collecting the condensed reaction products,
   wherein neither the metallic silicon, nor the copper based catalyst, nor the silicon-catalyst mixture is subjected to any washing step comprising any acid or other preparatory solution, including a hydrofluoric acid (HF) washing step.

2. The method according to claim 1, wherein the method has a selectivity for trialkoxysilane of greater than about 95%.

3. The method according to claim 1, wherein the copper based catalyst is present at a catalyst loading concentration of about 2 wt. % to about 10 wt. % by weight of the silicon-catalyst mixture.

4. The method according to claim 3, wherein the copper based catalyst is present at a catalyst loading of less than about 5 wt. % by weight of the silicon-catalyst mixture.

5. The method according to claim 1, wherein the $C_1$-$C_4$ alcohol is anhydrous.

6. The method according to claim 1, wherein the $C_1$-$C_4$ alcohol is ethanol.

7. The method according to claim 1, wherein the activation temperature is about 220° C.

8. The method according to claim 1, wherein the packed reactor is heated at an activation temperature of about 220° C. for a period of about 2-5 hours.

9. The method according to claim 1, wherein the reaction temperature is about 200° C.-about 240° C.

10. The method according to claim 9, wherein the reaction temperature is about 220° C.

11. The method according to claim 9, wherein the reaction temperature is about 240° C.

12. The method according to claim 1, wherein the alcohol has a residence time of about 9 minutes to about 71 minutes in the reactor.

13. A direct solvent free method for the synthesis of triethoxysilane, the method having a selectivity for triethoxysilane of greater than about 90%, the method comprising the steps of:
   providing a mixture of metallic silicon and copper based catalyst in a packed bed reactor at a catalyst loading of less than about 5 wt. % by weight of the silicon-catalyst mixture, wherein the copper based catalyst is selected from the group consisting of copper (I) chloride, copper (II) hydroxide, copper (II) oxide, and mixtures thereof;

heating the mixture at an activation temperature of about 220° C.;

introducing anhydrous ethanol to the reactor such that the ethanol has a residence time of about 35 minutes to about 71 minutes in the reactor, a reaction temperature of about 220° C.-about 240° C.;

condensing the reaction products in a heat exchanger; and collecting the condensed reaction products, wherein neither the metallic silicon, nor the copper based catalyst, nor the silicon-catalyst mixture is subjected to any washing step comprising any acid or other preparatory solution, including a HF washing step.

* * * * *